United States Patent
Rommel (10) Patent No.: US 9,117,564 B2
(45) Date of Patent: Aug. 25, 2015

(54) VARIABLE ANGLE COLLIMATOR

(71) Applicant: American Science and Engineering, Inc., Billerica, MA (US)

(72) Inventor: Martin Rommel, Lexington, MA (US)

(73) Assignee: American Science and Engineering, Inc., Billerica, MA (US)

(*) Notice: Subject to any disclaimer, the term of this patent is extended or adjusted under 35 U.S.C. 154(b) by 207 days.

(21) Appl. No.: 13/933,601

(22) Filed: Jul. 2, 2013

(65) Prior Publication Data

US 2014/0010351 A1 Jan. 9, 2014

Related U.S. Application Data

(60) Provisional application No. 61/668,268, filed on Jul. 5, 2012.

(51) Int. Cl.
 G21K 1/02 (2006.01)
 G21K 5/04 (2006.01)
 A61B 6/06 (2006.01)
 H01J 35/30 (2006.01)

(52) U.S. Cl.
 CPC ... G21K 1/02 (2013.01); A61B 6/06 (2013.01); G21K 5/04 (2013.01); H01J 35/30 (2013.01)

(58) Field of Classification Search
 CPC .......... A61B 6/032; A61B 6/035; A61B 6/06; A61B 6/4021; A61B 6/4028; A61B 6/4064; A61B 6/4071; H01J 35/24; H01J 35/30; G01N 23/046; G21K 1/02; G21K 1/025; G21K 1/04; G21K 5/04
 See application file for complete search history.

(56) References Cited

U.S. PATENT DOCUMENTS

| | | | | |
|---|---|---|---|---|
| 3,780,291 A | 12/1973 | Stein et al. | ...................... | 250/363 |
| 3,894,234 A * | 7/1975 | Mauch et al. | ................. | 378/146 |
| 4,031,401 A | 6/1977 | Jacob | ............................ | 250/503 |
| 4,045,672 A | 8/1977 | Watanabe | ..................... | 250/360 |
| 4,079,259 A | 3/1978 | Blum | ............................ | 250/505 |

(Continued)

FOREIGN PATENT DOCUMENTS

| | | | | |
|---|---|---|---|---|
| DE | 10 2005 029 674 | 12/2006 | ............... | G21K 1/02 |
| DE | 10 2008 025 109 | 12/2009 | ............... | G21K 1/02 |
| WO | WO 2011/069770 | 6/2011 | ............... | G21K 1/02 |

OTHER PUBLICATIONS

Wrobel et al., "X-ray backscattering: Variable irradiation geometry facilitates new insights," *18th World Conference of Non Destructive Testing* (Durban, South Africa), 7 pages, Apr. 16-20, 2012.

(Continued)

*Primary Examiner* — Thomas R Artman
(74) *Attorney, Agent, or Firm* — Sunstein Kann Murphy & Timbers LLP (57) ABSTRACT

A system for producing a controllable beam of radiation is controllable electronically, and includes no parts that must move relative to one another while in operation to form the beam. The direction and cross-section of the beam may be controlled electronically by controlling an electron beam. Various embodiments provide an X-ray collimator that allows forming a scanning X-ray beam of desired size and flux independently of the aperture material thickness without requiring movement of the aperture or physical components that create the aperture. Some embodiments provide an X-ray collimator that allows forming a scanning X-ray beam of desired size and flux independently of the beam angle.

16 Claims, 7 Drawing Sheets

(56) References Cited

U.S. PATENT DOCUMENTS

| | | | |
|---|---|---|---|
| 4,419,585 A | 12/1983 | Strauss et al. | 250/505.1 |
| 4,769,829 A * | 9/1988 | Webb et al. | 378/19 |
| 4,995,066 A | 2/1991 | Harding et al. | 378/146 |
| 5,038,370 A * | 8/1991 | Harding et al. | 378/146 |
| 5,493,596 A * | 2/1996 | Annis | 378/57 |
| 6,356,620 B1 | 3/2002 | Rothschild et al. | 378/146 |
| 7,688,937 B2 * | 3/2010 | Schomberg | 378/10 |
| 8,576,989 B2 * | 11/2013 | Kaminski | 378/160 |
| 2008/0089478 A1 | 4/2008 | Hartick et al. | 378/57 |
| 2009/0040520 A1 | 2/2009 | Misawa et al. | 356/326 |
| 2011/0096973 A1 | 4/2011 | Ding et al. | 382/131 |
| 2011/0293072 A1 | 12/2011 | Kaminski | 378/160 |
| 2014/0010351 A1 * | 1/2014 | Rommel | 378/64 |

OTHER PUBLICATIONS

Korean Intellectual Property Office, as International Searching Authority, International Search Report—International Application No. PCT/US2013/049098, dated Oct. 18, 2013, together with the Written Opinion of the International Searching Authority, 9 pages.

* cited by examiner

VARIABLE ANGLE COLLIMATOR

CROSS REFERENCE TO RELATED APPLICATIONS

This patent application claims priority from provisional U.S. patent application No. 61/668,268, filed Jul. 5, 2012, entitled, "Variable Angle Collimator," and naming Martin Rommel as inventor [practitioner's file 1945/B62], the disclosure of which is incorporated herein, in its entirety, by reference.

TECHNICAL FIELD

The present invention relates to X-ray sources, and more particularly to collimators.

BACKGROUND ART

X-ray backscatter imaging relies on scanning an object with a well collimated beam, often referred to as "pencil beam". In the past these beams had also been widely used for X-ray transmission imaging, but today fan and cone beams in conjunction with pixelated detectors dominate transmission imaging.

Figure 1A:
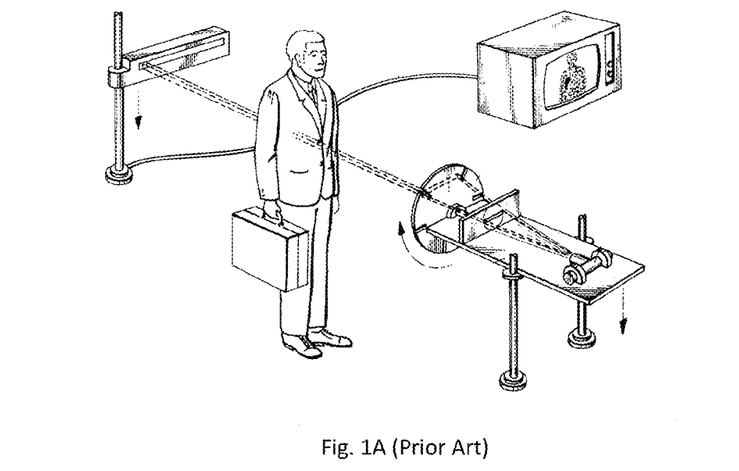
FIGS. 1A-1C schematically illustrate a prior art collimators.

There are two commonly used approaches for forming the collimated scanning beam. Both rely on a stationary X-ray source and a moving aperture. In both cases the radiation from a stationary X-ray source is first collimated into a fan beam by a stationary collimator. Then a moving part with an opening forms the scanning beam. This moving part is either a rotating disk with radial slits or a wheel with openings at the perimeter. The rotating disk covers the fan beam and the scanning beam is formed by the radiation emitted through the slits traversing the length of the fan beam opening. This approach is illustrated, e.g., in the 1973 U.S. Pat. No. 3,780,291 by Stein and Swift; see FIG. 1A. In the other approach a wheel with radial bores spinning around the X-ray source constitutes the moving part. If the source is placed at the center of the wheel the scanning beam is emitted in radial direction with the angular speed of the wheel.

Other approaches for forming a collimated beam from a stationary X-ray source have been proposed, for instance based on a rotating cylinder with a spiral groove as described by Annis in the 1996 U.S. Pat. No. 5,493,596.

Figure 1B:
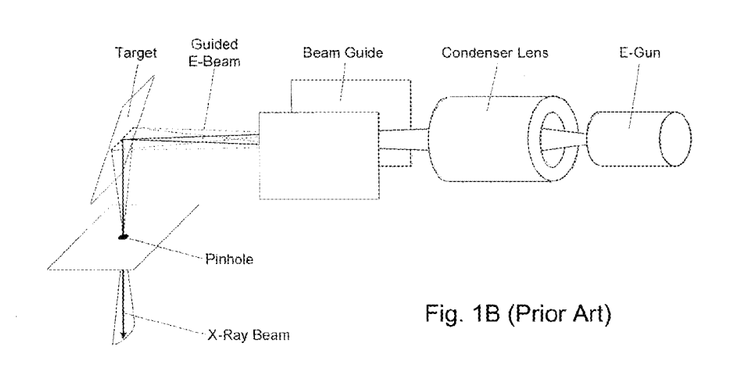

System configurations with moving X-ray sources have been developed. The motion of the X-ray source is typically not formed by moving the X-ray tube but by moving (scanning) the electron beam along an extended anode. This produces a moving X-ray source point (focal spot of the electron beam) the location of which can be electronically controlled. A moving X-ray source point enables the formation of the scanning X-ray beam with a simple stationary aperture (pinhole) at some distance from the source point. As the X-ray source point is moved from one end of the scan path to the other the scanning X-ray beam emerging form the aperture spans an angular range. An embodiment of this concept is, e.g., part of the system described in the 1977 U.S. Pat. No. 4,045,672 by Watanabe, see also FIG. 1B.

As the X-ray beam covers the angular range the cross-sectional area of the beam varies as the cosine of the angle between the beam and the normal of the aperture plane. If the angular range is small the beam variation is limited and may be neglected. If, however, a large angular range is needed the effect becomes significant. For instance, for a 120° angular range an off-normal angle of 60° at the extremes leads to at least a 50% reduction in beam size and delivered flux, as the cosine of 60° is one half In reality the beam variation is even larger as the material with the pinhole has a finite thickness which leads to a further reduction in beam cross-sectional area with increasing angle. This problem becomes more serious for X-rays of higher energies which require thicker shielding material for the material with the pinhole.

Figure 1C:
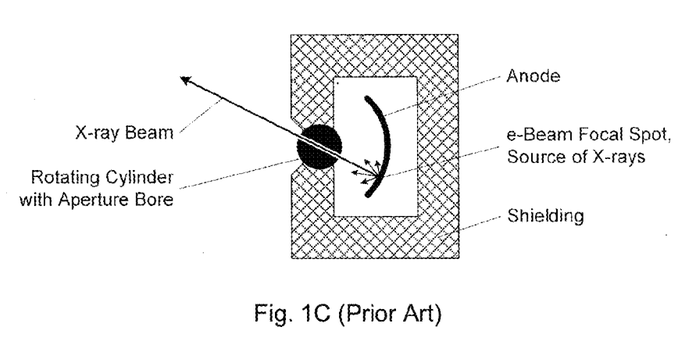

To allow for thick shielding material and to avoid the angular variation it has been suggested to replace the pinhole with a rotating cylinder containing a bore perpendicular through the axis as described in the 2002 U.S. Pat. No. 6,356,620 by Rothschild and Grodzins, see also FIG. 1C. This cylinder would have to rotate synchronously with the scanning electron beam so that the moving X-ray source point is aligned with the bore at any time. This approach solves both of the problems with the simple pinhole design: It forms a beam of constant size independently of the beam angle and does not limit the thickness of the material forming the aperture. However, this active solution introduces significant cost and complexity in comparison to the passive pinhole. It also largely eliminates the great flexibility offered by the electronic control of the electron beam.

Summary of the Embodiments

A variable angle collimator controllably produces a collimated beam of radiation without physically manipulating any member of the collimator. The angle of the collimated beam may be completely electronically controlled through control of an electron beam striking an anode.

In a first embodiment, a system for producing a steerable beam of radiation includes a radiation source configured to produce radiation at an angle, relative to a collimator, wherein the angle is electronically controllable; a collimator comprising material opaque to the radiation produced by the radiation source, the collimator comprising an aperture configured to receive radiation from the radiation source at a plurality of incident angles, and configured to pass a portion of the radiation through the collimator at each of the plurality of incident angles, so as to form a collimated beam of radiation having a beam cross-section, and wherein the collimator and radiation source are configured to remain stationary with respect to one another when producing a steerable beam of radiation.

The radiation source may include an electron source and an anode, configured such that the electron source illuminates the anode with an electronically steerable beam of electrons, so as to produce a movable point source of radiation.

The aperture, and therefore a cross-section of the resulting radiation beam, may have any of a variety of shapes, such as rhombus-shaped, square, and rectangular. In some embodiments, the shape of the aperture (and therefore the cross-section of the resulting beam) is variable as a function of the angle of the incident radiation relative to the aperture.

Various embodiments of the collimator present a variety of structures. For example, in one embodiment the collimator includes several surfaces, and the aperture is a compound aperture formed by cooperation between a first aperture in a first collimator surface and a second aperture in a second collimator surface. For example, the first surface may be a surface of a first plate, and the second surface may be a surface of a second plate disposed parallel to the first plate.

Another embodiment of a collimator includes a first member having a first surface, the first surface being one of a hyperbolic paraboloid surface or a modified hyperbolic paraboloid surface; and a second member having a second surface, the second surface being one of a hyperbolic paraboloid surface or a modified hyperbolic paraboloid surface; the first member disposed relative to the second member such that the first surface faces the second surface, the first surface and second surface separated by a gap so as to define a aperture through the collimator. In some embodiments, the collimator is a helically cut cylinder.

A method of irradiating a target with a collimated beam of radiation includes providing a steerable source of radiation configured to illuminate a collimator; providing a collimator comprising a hyperbolic paraboloid aperture having an input and an output, the collimator disposed in a fixed location relative to the steerable source of radiation; producing a collimated beam of radiation at a plurality of exit angles by: illuminating the input of the hyperbolic paraboloid aperture with illuminating radiation from a first illumination angle, such that a portion of the illuminating radiation passes through the collimator and exits the collimator at a first exit angle; and illuminating the input of the hyperbolic paraboloid aperture with illuminating radiation from a second illumination angle, the second illumination angle different from the first illumination angle, such that a portion of the illuminating radiation passes through the collimator and exits the collimator at a second exit angle, the second exit angle different from the first exit angle, such that radiation exiting the collimator at the first angle and at the second angle irradiate the target.

The step of providing a collimator may include proving a collimator having an input plate having an first face and a second face, and an first elongated aperture completely through the input plate between the first face and the second face; and an output plate having a third face and a fourth face, and an second elongated aperture completely through the output plate between the third face and the fourth face, the first face parallel to the fourth face, and separated from the fourth face by a predetermined distance, such that a projection of the first elongated aperture intersects the second elongated aperture at a non-zero angle, and such that the intersection of the projection of first elongated aperture and the second elongated aperture forms a rhombus-shaped aperture through which radiation may pass without contacting the input plate and without contacting the output plate.

Alternately, the stop of providing a collimator may include providing a collimator includes proving a collimator having: a first member comprising a first surface, the first surface being one of a hyperbolic paraboloid surface or a modified hyperbolic paraboloid surface; and a second member comprising a second surface, the second surface being one of a hyperbolic paraboloid surface or a modified hyperbolic paraboloid surface; the first member disposed relative to the second member such that the first surface faces the second surface, the first surface and second surface separated by a gap so as to define a hyperbolic paraboloid aperture through the collimator.

In some embodiments, producing a collimated beam at the first angle includes producing a collimated beam having a first shape in cross-section, producing a collimated beam at the second angle includes producing a collimated beam having a second shape in cross-section, wherein the second shape is different than the first shape.

In another embodiment, a system for producing a steerable beam of radiation includes radiation source means for producing an electronically steerable point source of illuminating radiation; and collimating means having an aperture configured to pass a portion of illuminating radiation incident on said collimating means; the radiation source means disposed, relative to the collimating means, so as to remain stationary with respect to the collimating means, and so as to illuminate the aperture with incident radiation from the steerable point source of radiation, such that the aperture produces a steerable beam of radiation.

The collimating means may include a first member comprising a first hyperbolic paraboloid surface; and a second member comprising a second hyperbolic paraboloid surface; wherein the first member is disposed, relative to the second member, such that the first hyperbolic paraboloid surface is disposed opposite the second hyperbolic paraboloid surface such that the first hyperbolic paraboloid surface is separated from the second hyperbolic paraboloid surface by an aperture gap, such that the first member and second member form the aperture across the aperture gap.

Alternately, the collimating means may include a first member comprising a first modified hyperbolic paraboloid surface; and a second member comprising a second modified hyperbolic paraboloid surface; wherein the first member is disposed, relative to the second member, such that the first modified hyperbolic paraboloid surface is disposed opposite the second modified hyperbolic paraboloid surface such that the first modified hyperbolic paraboloid surface is separated from the second modified hyperbolic paraboloid surface by an aperture gap, wherein the aperture gap is not constant, such that the first member and second member form the aperture across the aperture gap.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Various embodiments provide an X-ray collimator that allows forming a scanning X-ray beam of desired size and flux independently of the aperture material thickness without requiring movement of the aperture or physical components that create the aperture. Some embodiments provide an X-ray collimator that allows forming a scanning X-ray beam of desired size and flux independently of the beam angle.

In various embodiments, a collimator of non-moving parts creates a beam (e.g., a pencil-beam) from a point-like radiation source in a way that the cross-sectional area of the pencil-beam varies with the incident angle in a deliberate way. In particular, some embodiments allow the creation pencil-beams with a cross-sectional area which is independent of the incident angle. In some embodiments, a variable angle collimator includes attenuating materials rigidly arranged such that radiation from a point-like source is effectively collimated into a beam (e.g., a pencil beam) for a range of incident angles and such that the cross-section of the beam is a function of the incident angle.

For example, the beam angle may be determined by controlling the focal point of a source electron beam impinging on an anode. Such an electron beam may be described as being "steerable." A source of an electron beam, together with an anode, may be described as a radiation source configured to produce radiation at an angle, relative to a collimator, wherein the angle is electronically controllable.

The focal point becomes an X-ray source. As such, controllably moving the electron beam provides control of the focal point, and thereby provides control of the location of X-ray source. Controlling the location of the X-ray source, in turn, provides control of the angle of which the X-rays impinge on the collimator, and thereby provide control of the direction of the X-ray beam from the collimator. These features provide the abilities to scan the produced X-ray beam in a step-wise fashion, and/or vary the scan speed, and/or vary the scan angle range, for example. Such an X-ray source may be described as being "controllable" or "steerable" in that its location (e.g., on an anode; and/or relative to an aperture in a collimator) may be electronically controlled.

A first embodiment of a collimator 200 is schematically illustrated by FIGS. 2A-2H, and includes a first plate 210 and a second plate 220. First plate 210 has a first face 210A and a second face 210B, and is opaque to the type of radiation for which the collimator 200 is intended. For example, if collimator 200 is intended to collimate X-rays, then the first plate 210 is opaque to X-rays.

First plate 210 includes an elongated aperture 211 that extends completely between the first face 210A and the second face 210B for the purpose of passing radiation to which the first plate 210 is otherwise opaque. In this embodiment, elongated aperture 211 has a rectangular shape, but other shapes may be used in various embodiments.

Collimator 200 also includes a second plate, 220, which has a first face 220C and a second face 220D, and also have an elongated aperture 221 that extends completely between the first face 220C and the second face 220D for the purpose of passing radiation to which the second plate 220 is otherwise opaque. In this embodiment, elongated aperture 221 has a rectangular shape, but other shapes may be used in various embodiments. When viewed as in FIGS. 2A and 2B, the apertures 211 and 221 are at different angles.

Figure 2A:
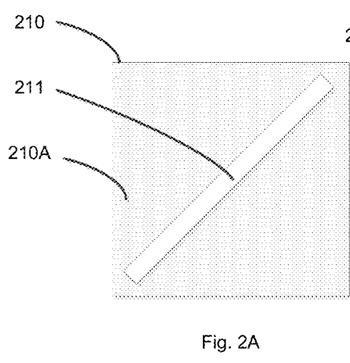
FIGS. 2A-2I schematically illustrate an embodiment of a collimator.
Figure 2B:
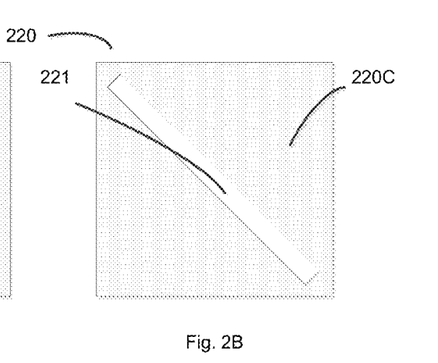
Figure 2C:
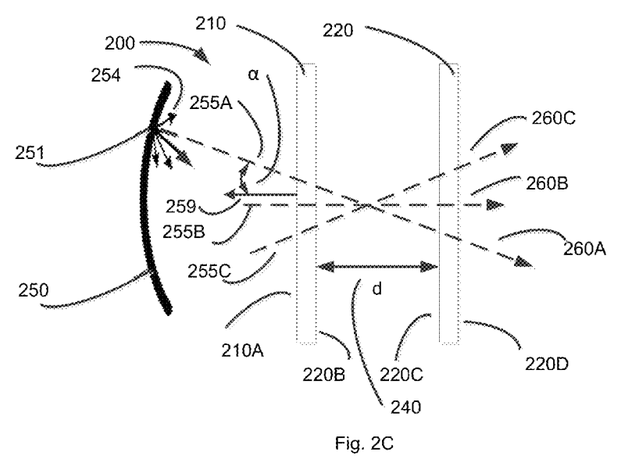

In collimator 200, the first plate 210 and the second plate 220 are disposed parallel to one another, and separated by a gap "d" 240, as schematically illustrated in FIG. 2C. The plates 210, 220 are arranged such that the elongated apertures are disposed at an angle relative to one another, for example such that a projection of elongated aperture 211 onto elongated aperture 221 forms an "X" shape. In some embodiments, elongated aperture 211 is arranged so that its projection onto elongated aperture 221 meets aperture 221 at right angles (e.g., "+")

In such configurations, the first plate 210 and second plate 220 block all radiation (254) from anode 250, except that the first aperture 211 and second aperture 221 cooperate to form a rhombus-shaped aperture through which some radiation may pass without contacting the first plate 210 (which may be known as an input plate) and without contacting the second plate 220 (which may be known as an output plate). More particularly, a projection of the first elongated aperture 211 intersects the second elongated aperture 221 at a non-zero angle and such that the intersection of the projection of first elongated aperture 211 and the second elongated aperture 221 forms a rhombus-shaped aperture through which radiation may pass without contacting input plate 210 and without contacting the output plate 220. In this way, all radiation impinging on the input plate 210 is blocked, except for that portion of impinging radiation that passes through the first elongated aperture 211. All of that radiation is, in turn, blocked by the second plate 220, except for that portion of the radiation that passes through the second elongated aperture 221. In other words, all impinging radiation is blocked by the collimator 200 except that radiation that happens to approach the collimator 200 at an angle that aligns with both the first elongated aperture 211 and the second elongated aperture 221. As such, the first elongated aperture 211 and the second elongated aperture 221 may be described as forming a compound aperture 270.

The inventor has discovered that the collimator 200 provides a useful feature, in that the compound aperture 270 formed by the cooperation of the first aperture 211 and second aperture 221 exists at a variety of angles with respect to impinging radiation. In other words, the collimator 200 will present a compound aperture (i.e., through the collimator 200) to radiation approaching the collimator 200 from a variety of directions, all without having to move or manipulate the first plate 210 and/or the second plate 220. Consequently, a collimated beam of radiation 260 exits the collimator 200, and the direction of that collimated beam varies as a function of the location of the source of the radiation.

More specifically, a source (which may be referred to a "point source") of radiation 251 illuminates collimator 200 from any of a number of positions. For example, in FIG. 2C, the source of radiation 250 is the focal point of an electron beam on anode 250. Radiation 254 departs from that point 251 at a variety of angles, but only some of that radiation, in this example radiation along vector 255A, approaches collimator 200 in a direction that will allow the radiation to pass through both the first aperture 211 and the second aperture 221, to yield collimated radiation beam 260A.

Figures 2D, 2E, 2F:
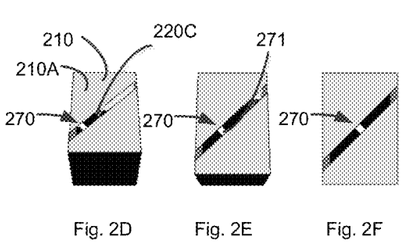
Figure 2G:
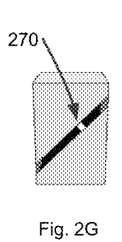

Illustrative examples of the compound aperture 270 formed by the cooperation of apertures 211 and 221 are schematically illustrated in FIGS. 2D-2H. In each figure, a collimated X-ray beam is formed from impinging radiation by the projected, rhombus-shaped intersection of the two apertures 211; 221 (which may also be known as slots) as seen from the source point (251) of the radiation. In FIG. 2F, the beam angle is normal to the collimator plates 210, 220 (i.e., the angle, a, between the vector of impinging radiation (e.g., 255B) and a vector normal to the surface 210A of plate 210, is zero) and the compound aperture 270 (and consequently the beam, e.g. 260B) is square-shaped. For reference, a non-zero beam angle, α, between a vector 259 normal to the surface 210A of plate 210 and beam vector 255A is schematically illustrated in FIG. 2C As the X-ray source point 251 moves up or down, the beam angle α changes and the height j (271; see for example FIG. 2I) of the aperture rhombus 270 is reduced like cos(α). At the same time the opening shifts laterally by 0.5 d tan(α) where d (240) is the distance between the collimator plates.

For example, as discussed above, when the impinging radiation is normal to the surface 210A of the collimator 200, the aperture 270 appears (from the point of the radiation source) near the center of the collimator 200. Alternately, when the impinging radiation approaches the surface 210A of the collimator 200 from another angle, the aperture appears (from the point of the radiation source) in a different location (e.g., off-center), as in FIGS. 2D, 2E, 2G, and 2H, for example. In this embodiment 200, if the beam angle varies between +45° and −45° the lateral range for the aperture shift would be equal to the distance between the plates d. In some embodiments, the path of the X-ray source point may be adjusted to compensate for the lateral shift of the aperture, so as to maintain a straight scan line.

Therefore, to control the collimated radiation beam, the direction of the electron beam may be changed or manipulated, by ways known in the art, such that the focal point 251 of the electron beam may be moved to a different location on the anode 250. Because the focal point 251 is the source of the radiation that illuminates collimator 200, the radiation source is effectively manipulated in this way, and radiation approaches the collimator 200 from a different angle. For example, the radiation focal point 251 may be moved to produce illuminating radiation along vector 255B or 255C. Indeed, the location of the focal point may be moved stepwise, or continuously, to produce radiation from a variety of directions. Each location of the focal point 241 therefore produces a collimated beam that exits the collimator 200 at an angle that varies as a function of the location of the focal point 251. For example, radiation along vector 255A produces collimated beam 260A; radiation along vector 255B produces collimated beam 260B; and radiation along vector 255C produces collimated beam 260C. As such, the direction of a collimated beam of radiation may be controlled electronically, without physically moving or manipulating a structural element of the collimator, and without physically moving or manipulating a structural element of the source of radiation.

Figure 3A:
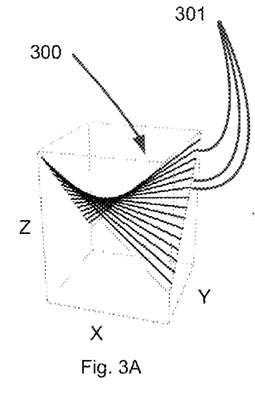
FIGS. 3A-C schematically illustrate a virtual hyperbolic paraboloid surface.
Figures 3B, 3C:
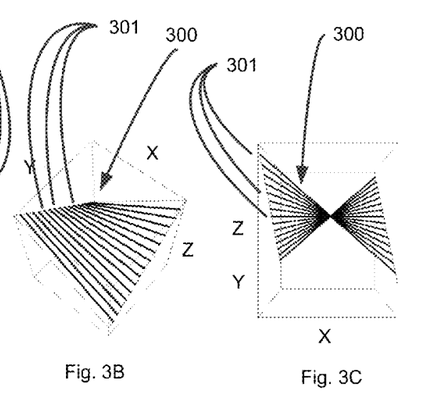

A virtual surface between the two slotted collimator plates 210, 220 to which the X-ray beam is confined, has the shape of a hyperbolic paraboloid, as defined by the function z(x,y)=xy. Such a virtual surface 300 is schematically illustrated in FIGS. 3A-3C, where the dark lines 301 depict possible beam positions.

Figures 2H, 2I:
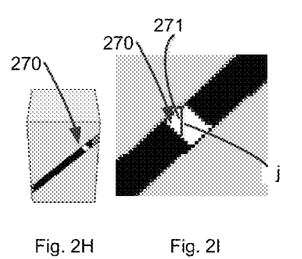
Figure 2J:
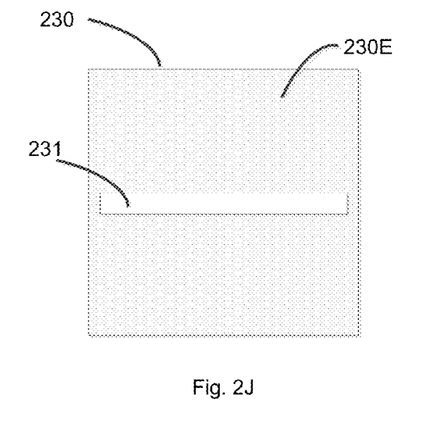
FIGS. 2J-2K schematically illustrate an embodiment of a collimator.
Figure 2K:
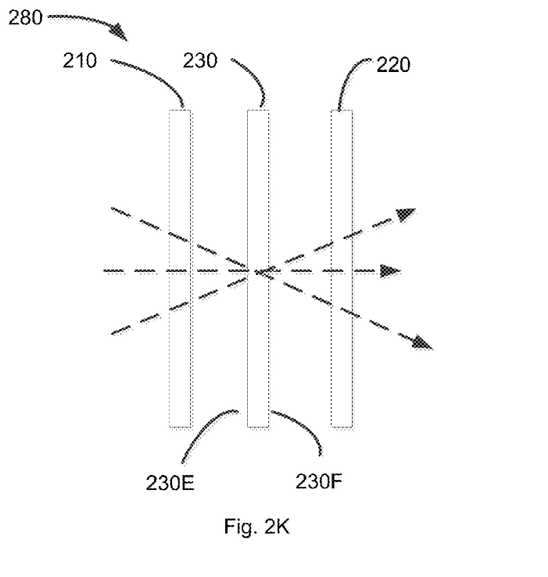

An alternate embodiment 280 is schematically illustrated in FIGS. 2J and 2K, and includes a third plate, or intermediate plate, 230. Plate 230 has a first face 230E and a second face 230F, and is opaque to the type of radiation for which the collimator 280 is intended. Intermediate plate 230 also has an aperture 231, and is disposed between plates 210 and 220 such that the virtual hyperbolic paraboloid surface 300 passes through aperture 231, and therefore forms a part of compound aperture 270 and thereby allows some radiation to pass through collimator 280. Such an embodiment may enhance the degree to which the collimator is opaque (i.e., the opacity of the collimator), and may further refine the collimated beam. In some embodiments, for example in a symmetric design for which the slot angles for beam entrance and exit are the same, a plate 230 in the center would have a horizontal slot 231.

Figure 4A:
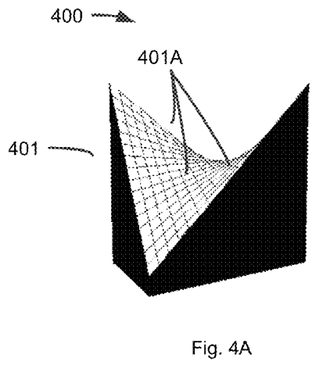
FIG. 4A-C schematically illustrate an embodiment a collimator.
Figure 4B:
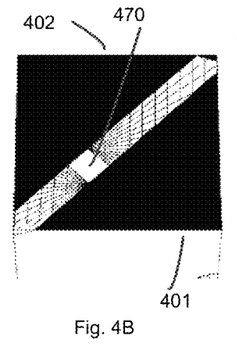
Figure 4C:
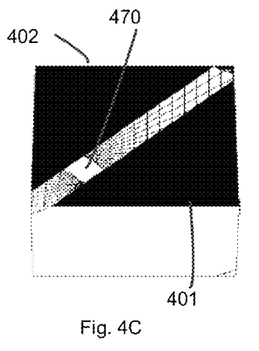

In another embodiment a collimator 400 is formed not by multiple plates but by two facing blocks 401, 402, each with a hyperbolic paraboloid surface as schematically illustrated in FIGS. 4A-4C. In other words, such an embodiment includes two real, instead of virtual, surfaces between the input and output apertures.

One such block 401 is schematically illustrated in FIG. 4A, and shows hyperbolic paraboloid surface 401A. The blocks 401, 402 cooperate to form an output aperture 470, similar to the compound aperture 270 formed by plates 210 and 220 discussed above. In short, the aperture 470 selectively passes radiation from a source, depending on the angle at which the radiation impinges on the collimator 400, such that the resulting collimated beam may be controlled by controlling the location of the radiation source. The apparent motion of such an aperture 470 is schematically illustrated by the different locations of the aperture 470 in FIG. 4B and FIG. 4C.

FIGS. 5A-5E schematically illustrate an embodiment of a helically cut cylinder collimator 500. Generally, this embodiment 500 is a variable-angle collimator that consists of a right circular cylinder 501 with a cylinder axis 503 and a slit 502. The slit 502 passes completely through cylinder 501, and twists along axis 503.

Figure 5A:
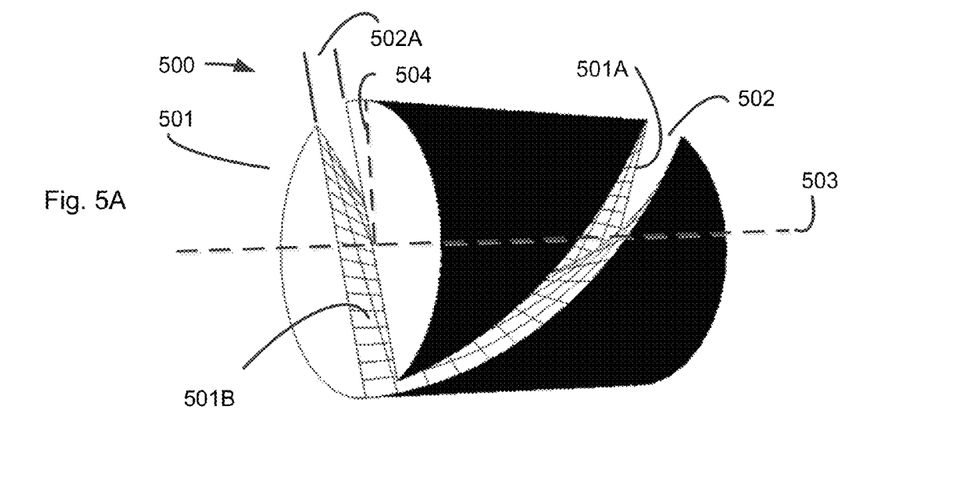
FIGS. 5A-5E schematically illustrate an embodiment of a helically cut cylinder collimator.
Figure 5B:
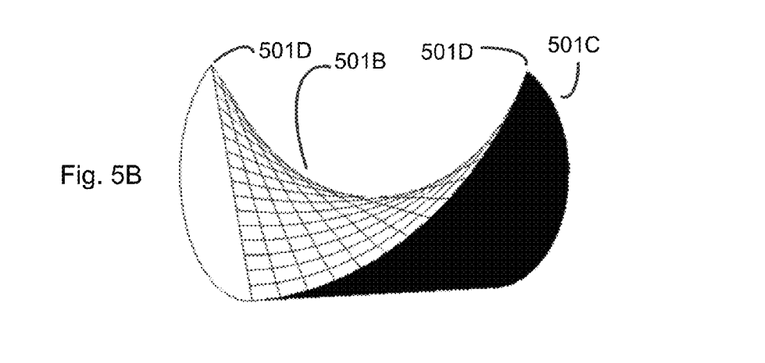

A cutaway view of an embodiment of collimator 500 is schematically illustrated in FIG. 5B, and shows bounding surface 501B. The bounding surface 501B and the cylinder surface 501C define slit edges 501D. In some embodiments, each of the slit edges 501D defines a helix about cylinder axis 503. As such, bounding surface 501B, being the surface between the helical edges 501D, may be described as a "helical surface." Surface 501A is also a helical surface, and as such, slit 502 may be described as a "helical slit." Stated alternately, slit 502 has a helical shape, such that the bounding surfaces 501A, 501B of the slit 502 form (or are spanned by) a double helix, as schematically illustrated in FIG. 5A.

In one embodiment, the slit 502 at the radius 504 of the cylinder 501 (i.e., at the surface 501C of the cylinder 501) forms a 45° angle 520 with the direction of the axis 503 of the cylinder 501, resulting in square shaped aperture 510. See, for example, slit 502 in FIG. 5D.

Figure 5C:
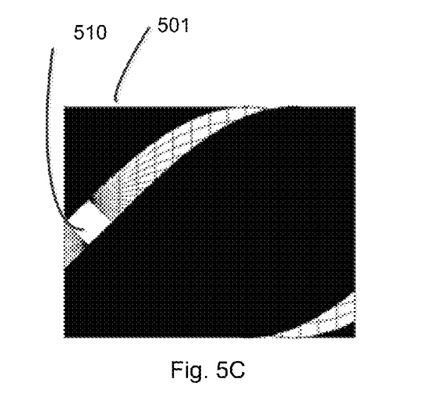
Figure 5D:
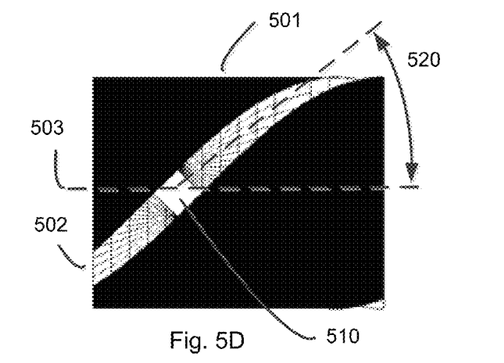
Figure 5E:
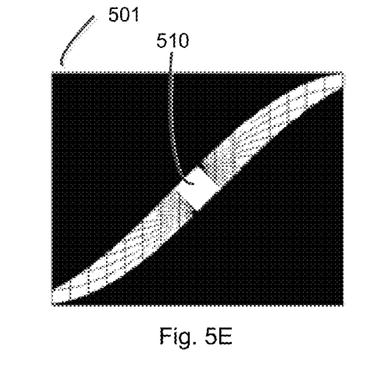

In some embodiments, slit 502 has a constant width 502A, which produces an angle-independent beam cross-section. For example, aperture 510 retains a square shape from a variety of angles, as schematically illustrated in FIGS. 5C-5E.

Figure 6A:
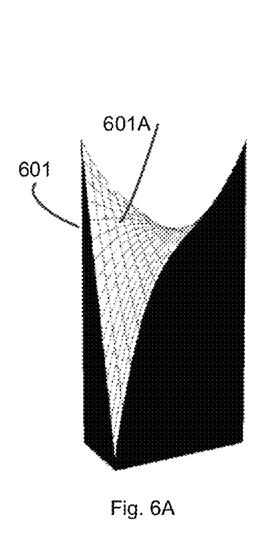
FIG. 6A-C schematically illustrate an embodiment of a collimator.
Figure 6B:
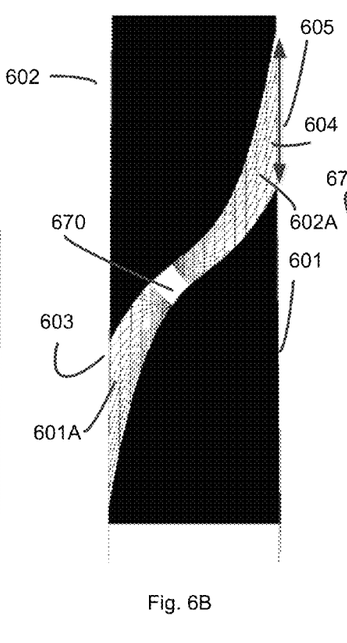
Figure 6C:
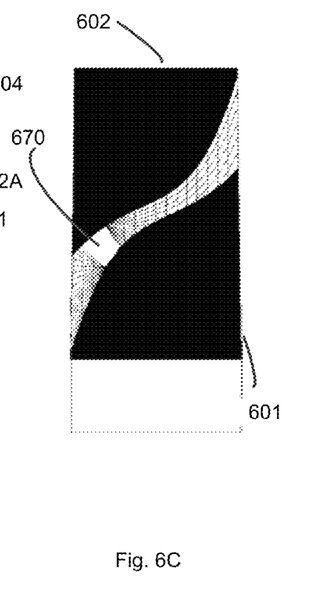

In another embodiment 600, schematically illustrated in FIGS. 6A-6C, the height h 605 of the gap 604 between the two surfaces 601A, 602A of two facing blocks 601, 602 forming the twisted collimator slit 603 is not constant as, such as in the embodiment 400 in FIGS. 4A-4C for example. Rather, the height h 605 of the gap 604 increases as the secant of the beam angle α:

$$h \propto sec(\alpha) = 1/\cos(\alpha)$$

In this way, an X-ray beam with constant cross-sectional area independent of the beam angle the hyperbolic paraboloid surface is maintained, because the square, or near-square, cross-section of the beam is maintained.

Relying on the angle-dependent height alone to modify the twisted collimator slit 603 leads to surfaces defined by:

$$z(x, y) = x \cdot y \pm \frac{h}{2}\sqrt{1+y^2}.$$

These surfaces maintain a constant height h of the beam cross-section; however the square shape obtained at α=0 (where α=0 is an angle that is normal to the surface of the collimator) is lost with increasing angle α. To maintain a square or near square cross-section of the beam the slope of the slots on the collimator's entrance and exit surfaces will have to increase as the beam angle increases. So the center surface of the slit will no longer be given by z(x,y)=x·y, but by:

$$z(x,y)=x \cdot \sin h(y)$$

or an approximation thereof. With the height given by $h\sqrt{1+y^2}$ the aperture will maintain a square shape but reduce in size with increasing angle. A height given by cos h(y) maintains a constant cross-sectional area.

The center surface (h=0) will remain linear in x as this is the direction of the straight beam. An example of the modified hyperbolic paraboloid surface is shown in FIGS. 6A-6C.

FIGS. 6B and 6C schematically illustrate a collimator 600 formed by two facing blocks 601, 602, which form output aperture 670.

Figure 2L:
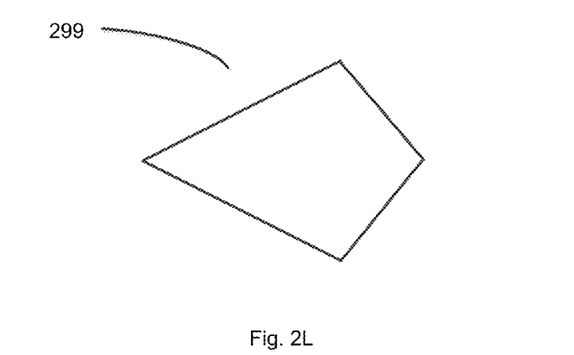
FIG. 2L schematically illustrates a cross-section of a collimated beam having a kite shape.

Modifying the hyperbolic paraboloid surfaces of the collimator not only allows achieving a beam angle independent beam cross-section area, but also allows the deliberate variation of the cross-section area as a function of the beam angle. Keeping the beam cross-section area constant is just one special case of controlling the area. Controlling the beam cross-section area as a function of the beam angle enables designs with modulated beam shapes and dose rate (flux) delivered by the collimated beam. In various embodiments, the contours of an aperture in a collimator may be configured to produce a beam cross-section of any of a variety of shapes, such as rhombus-shaped (e.g., rhombus aperture 270 of FIG. 21), rectangular or square-shaped (e.g., square aperture 10 of FIG. 5C), or even kite-shaped (e.g., aperture 299 of FIG. 2L), to name but a few examples. In general, the aperture of a collimator may be configured to produce a beam with a size and shape (cross-section) in a manner deemed, by a system designer, to be beneficial to the application for which the system is designed.

Figure 7:
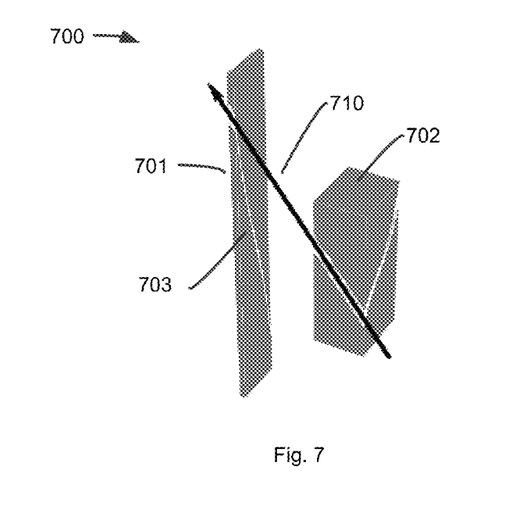
FIG. 7 schematically illustrates an embodiment of a collimator block with a modified hyperbolic paraboloid surface and a secondary plate.

In comparison to a pinhole collimator, various embodiments may produce increased scatter which can be reduced by increasing the thickness of the collimator (e.g., collimator 400) or, more effectively, by adding one or more additional secondary plates on the exit side of the collimator. Such an embodiment 700 is schematically illustrated in FIG. 7, and includes a plate 701 adjacent to collimator 702. Collimator 702 may be any of the collimators described above in connection with FIGS. 2A-6C, for example. The slot in plate 701 includes an aperture 703 disposed to clear the path of the primary beam 710 exiting from a collimator 702.

A system for producing a collimated beam of radiation may be described as having a source of radiation, and a collimator according one of the embodiments described above, and circuits for controlling the source of radiation so as to control the angle at which radiation from the source impinges on the collimator. A method of producing a controllable collimated beam of radiation may include providing a providing a collimator according one of the embodiments described above, and then illuminating the collimator with radiation from the radiation source from a variety of angles, so as to control the angle of the collimated beam exiting the collimator.

Some embodiments provide a variable angle collimator including an input plate having a first face and a second face, and an first elongated aperture completely through the input plate between the first face and the second face; an output plate having a third face and a fourth face, and an second elongated aperture completely through the output plate between the third face and the fourth face, the first face parallel to the fourth face, and separated from the fourth face by a predetermined distance, such that a projection of the first elongated aperture intersects the second elongated aperture at a non-zero angle and such that the intersection of the projection of first elongated aperture and the second elongated aperture forms a rhombus-shaped aperture through which radiation may pass without contacting the input plate and without contacting the output plate.

In some embodiments, the non-zero angle is a right angle.

Some embodiments also include an intermediate plate having a third aperture completely through the intermediate plate. The intermediate plate is disposed between the input plate and the output plate such that the third aperture aligns with the first elongated aperture and the second elongated aperture at a plurality of angles, such that the first elongated aperture, the second elongated aperture and the third aperture form a rhombus-shaped aperture (or an aperture of another polygonal shape) through which radiation may pass without contacting any of the input plate, the output plate and the intermediate plate. In some embodiments, the third aperture is an elongated aperture, and in some embodiments, the third aperture is a rectangular aperture.

Another embodiment of a variable angle collimator includes a first member having a first surface, the first surface being one of a hyperbolic paraboloid surface or a modified hyperbolic paraboloid surface, and a second member also having a first surface, the first surface being one of a hyperbolic paraboloid surface or a modified hyperbolic paraboloid surface. The first member is disposed relative to the second member such that the first surface faces the second surface, and is separated from the second surface separated by a gap, so as to define a hyperbolic paraboloid aperture through the collimator.

In some embodiments, the first surface is a modified hyperbolic paraboloid surface and the second surface is a modified hyperbolic paraboloid surface, such that the gap between the first surface and the second surface is not constant.

In another embodiment, a radiation scanning system includes a source of radiation configured to controllably provide a beam of radiation at a plurality of angles, and a collimator having a hyperbolic paraboloid aperture having an input and an output. In some embodiments, the collimator includes an input plate having a first face and a second face, and an first elongated aperture completely through the input plate between the first face and the second face; an output plate having a third face and a fourth face, and an second elongated aperture completely through the output plate between the third face and the fourth face, the first face parallel to the fourth face, and separated from the fourth face by a predetermined distance, such that a projection of the first elongated aperture intersects the second elongated aperture at a non-zero angle, such that the intersection of the projection of first elongated aperture and the second elongated aperture forms a rhombus-shaped aperture through which radiation from the source of radiation, at a plurality of angles, may pass without contacting the input plate and without contacting the output plate.

In some embodiments, the collimator includes a first member having a first surface, the first surface being one of a hyperbolic paraboloid surface or a modified hyperbolic paraboloid surface, and a second member having a second surface, the second surface being one of a hyperbolic paraboloid surface or a modified hyperbolic paraboloid surface. The first member disposed relative to the second member such that the first surface faces the second surface, and is separate from the second surface by a gap so as to define a hyperbolic paraboloid aperture through the collimator.

A method of irradiating a target with a collimated beam of radiation includes providing a collimator having a hyperbolic paraboloid aperture having an input and an output; illuminating the input of the hyperbolic paraboloid aperture with illuminating radiation from a first illumination angle, such that a portion of the illuminating radiation passes through the collimator and exits the collimator through the fourth surface at a first exit angle; illuminating the input of the hyperbolic paraboloid aperture with illuminating radiation from a second illumination angle, such that a portion of the illuminating radiation passes through the collimator and exits the collimator through the fourth surface at a second exit angle, the second exit angle different from the first exit angle.

In some embodiments, providing a collimator includes proving a collimator having an input plate having an first face and a second face, and an first elongated aperture completely through the input plate between the first face and the second face; an output plate having a third face and a fourth face, and an second elongated aperture completely through the output plate between the third face and the fourth face, the first face parallel to the fourth face, and separated from the fourth face by a predetermined distance, such that a projection of the first elongated aperture intersects the second elongated aperture at a non-zero angle, and such that the intersection of the projection of first elongated aperture and the second elongated aperture forms a rhombus-shaped aperture through which radiation may pass without contacting the input plate and without contacting the output plate.

In some embodiments, providing a collimator includes providing a collimator having a first member having a first surface, the first surface being one of a hyperbolic paraboloid surface or a modified hyperbolic paraboloid surface; a second member having a second surface, the second surface being one of a hyperbolic paraboloid surface or a modified hyperbolic paraboloid surface; such that the first member is disposed relative to the second member such that the first surface faces the second surface, the first surface and second surface separated by a gap so as to define a hyperbolic paraboloid aperture through the collimator.

In another embodiment, there is provided a variable angle collimator having a cylindrical housing, the housing having a cylindrical surface and an axis, and comprising helical slit passing completely through the housing, wherein the helical slit defines a first bounding surface and a second bounding surface, the first bounding surface separated from the second bounding surface by a gap. In some embodiments, the gap is a constant distance between the first bounding surface and the second bounding surface at the cylindrical surface.

Definitions. As used in this description and the accompanying claims, the following terms shall have the meanings indicated, unless the context otherwise requires:

A hyperbolic paraboloid surface is a surface defined by the following formula, where z is the height of the gap between opposing surfaces defining an aperture, and x and y are coordinates on orthogonal axes in a plane normal to z:

$$\frac{z}{c} = \frac{y^2}{b^2} - \frac{x^2}{a^2}.$$

In some embodiments, a hyperbolic paraboloid surface is defined by the following form of the foregoing formula:

$$z(x,y)=x \cdot y$$

A modified hyperbolic paraboloid surface is a hyperbolic paraboloid surface modified as described in connection with FIG. 7.

A hyperbolic paraboloid aperture is a passage through a collimator, the passage having at least one contour in the shape of a hyperbolic paraboloid surface or a modified hyperbolic paraboloid surface.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed (prefaced with the letter "P" so as to avoid confusion with the actual claims presented below) includes:

P1. A variable angle collimator comprising: an input plate having a first face and a second face, and an first elongated aperture completely through the input plate between the first face and the second face; an output plate having a third face and a fourth face, and an second elongated aperture completely through the output plate between the third face and the fourth face, the first face parallel to the fourth face, and separated from the fourth face by a predetermined distance, such that a projection of the first elongated aperture intersects the second elongated aperture at a non-zero angle and such that the intersection of the projection of first elongated aperture and the second elongated aperture forms a rhombus-shaped aperture through which radiation may pass without contacting the input plate and without contacting the output plate.

P2. The variable angle collimator of potential claim P1, wherein the non-zero angle is a right angle.

P3. The variable angle collimator of potential claim P1, further comprising an intermediate plate having a third aperture completely through the intermediate plate, the intermediate plate disposed between the input plate and the output plate such that the third aperture aligns with the first elongated aperture and the second elongated aperture at a plurality of angles, such that the first elongated aperture, the second elongated aperture and the third aperture form a rhombus-shaped aperture through which radiation may pass without contacting any of the input plate, the output plate and the intermediate plate.

P4. The variable angle collimator of potential claim P3, wherein the third aperture is an elongated aperture.

P5. The variable angle collimator of potential claim P3, wherein the third aperture is a rectangular aperture.

P6. A variable angle collimator comprising: a first member comprising a first surface, the first surface being one of a hyperbolic paraboloid surface or a modified hyperbolic paraboloid surface; a second member comprising a second surface, the second surface being one of a hyperbolic paraboloid surface or a modified hyperbolic paraboloid surface; the first member disposed relative to the second member such that the first surface faces the second surface, the first surface and second surface separated by a gap so as to define a hyperbolic paraboloid aperture through the collimator.

P7. The variable angle collimator according to potential claim P6, wherein the first surface is a modified hyperbolic paraboloid surface and the second surface is a modified hyperbolic paraboloid surface, such that the gap between the first surface and the second surface is not constant.

P11. A radiation scanning system comprising: a source of radiation configured to controllably provide a beam of radiation at a plurality of angles; a collimator comprising a hyperbolic paraboloid aperture having an input and an output.

P12. The radiation scanning system of potential claim P11, wherein the collimator comprises: an input plate having a first face and a second face, and an first elongated aperture completely through the input plate between the first face and the second face; an output plate having a third face and a fourth face, and an second elongated aperture completely through the output plate between the third face and the fourth face, the first face parallel to the fourth face, and separated from the fourth face by a predetermined distance, such that a projection of the first elongated aperture intersects the second elongated aperture at a non-zero angle, such that the intersection of the projection of first elongated aperture and the second elongated aperture forms a rhombus-shaped aperture through which radiation from the source of radiation, at a plurality of angles, may pass without contacting the input plate and without contacting the output plate.

P13. The radiation scanning system of potential claim P11, wherein the collimator comprises: a first member comprising a first surface, the first surface being one of a hyperbolic paraboloid surface or a modified hyperbolic paraboloid surface; a second member comprising a second surface, the second surface being one of a hyperbolic paraboloid surface or a modified hyperbolic paraboloid surface; the first member disposed relative to the second member such that the first surface faces the second surface, the first surface and second surface separated by a gap so as to define a hyperbolic paraboloid aperture through the collimator.

P21. A method of irradiating a target with a collimated beam of radiation, the method comprising: providing a collimator comprising a hyperbolic paraboloid aperture having an input and an output; illuminating the input of the hyperbolic paraboloid aperture with illuminating radiation from a first illumination angle, such that a portion of the illuminating radiation passes through the collimator and exits the collimator through the fourth surface at a first exit angle; illuminating the input of the hyperbolic paraboloid aperture with illuminating radiation from a second illumination angle, such that a portion of the illuminating radiation passes through the collimator and exits the collimator through the fourth surface at a second exit angle, the second exit angle different from the first exit angle.

P22. The method of irradiating a target with a collimated beam of radiation according to potential claim P21, wherein providing a collimator includes proving a collimator having: an input plate having an first face and a second face, and an first elongated aperture completely through the input plate between the first face and the second face; an output plate having a third face and a fourth face, and an second elongated aperture completely through the output plate between the third face and the fourth face, the first face parallel to the fourth face, and separated from the fourth face by a predetermined distance, such that a projection of the first elongated aperture intersects the second elongated aperture at a non-zero angle, and such that the intersection of the projection of first elongated aperture and the second elongated aperture forms a rhombus-shaped aperture through which radiation may pass without contacting the input plate and without contacting the output plate.

P23. The method of irradiating a target with a collimated beam of radiation according to potential claim P21, wherein providing a collimator includes proving a collimator having: a first member comprising a first surface, the first surface being one of a hyperbolic paraboloid surface or a modified hyperbolic paraboloid surface; a second member comprising a second surface, the second surface being one of a hyperbolic paraboloid surface or a modified hyperbolic paraboloid surface; the first member disposed relative to the second member such that the first surface faces the second surface, the first surface and second surface separated by a gap so as to define a hyperbolic paraboloid aperture through the collimator.

P31. A variable angle collimator comprising: a cylindrical housing, the housing having a cylindrical surface and an axis, and comprising helical slit passing completely through the housing, the helical slit having a first bounding surface and a second bounding surface, the first bounding surface separated from the second bounding surface by a gap.

P32. The variable angle collimator of potential claim P31, wherein the gap being a constant distance between the first bounding surface and the second bounding surface at the cylindrical surface.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A system for producing a steerable beam of radiation, comprising:
    a radiation source configured to produce radiation at an angle, relative to a collimator, wherein the angle is electronically controllable; and
    a collimator comprising material opaque to the radiation produced by the radiation source, the collimator comprising an aperture configured to receive radiation from the radiation source at a plurality of incident angles, and configured to pass a portion of the radiation through the collimator at each of the plurality of incident angles, so as to form a collimated beam of radiation having a beam cross-section, the collimator comprising:
        a first member comprising a first surface, the first surface being one of a hyperbolic paraboloid surface or a modified hyperbolic paraboloid surface; and
        a second member com risin a second surface the second surface being one of a hyperbolic paraboloid surface or a modified hyperbolic paraboloid surface;
        the first member disposed relative to the second member such that the first surface faces the second surface, the first surface and second surface separated by a gap so as to define the aperture through the collimator;
    wherein the collimator and radiation source are configured to remain stationary with respect to one another when producing a steerable beam of radiation.

2. The system of claim 1 wherein the radiation source comprises an electron source and an anode, the electrode source configured to illuminate the anode with a steerable beam of electrons, so as to produce a movable point source of radiation.

3. The system of claim 1 wherein the aperture has a rhombus shape.

4. The system of claim 1 wherein the aperture has a square shape.

5. The system of claim 1 wherein the shape of the aperture is variable as a function of the incident angle of the radiation relative to the aperture.

6. The system of claim 1, wherein the first surface is a modified hyperbolic paraboloid surface and the second surface is a modified hyperbolic paraboloid surface, such that the gap between the first surface and the second surface is not constant.

7. The system of claim 1, wherein the collimator is a helically cut cylinder.

8. A method of irradiating a target with a collimated beam of radiation, the method comprising:
    providing a steerable source of radiation configured to illuminate a collimator;
    providing a collimator comprising a hyperbolic paraboloid aperture having an input and an output, the collimator disposed in a fixed location relative to the steerable source of radiation;
    producing a collimated beam of radiation at a plurality of exit angles by:

illuminating the input of the hyperbolic paraboloid aperture with illuminating radiation from a first illumination angle, such that a portion of the illuminating radiation passes through the collimator and exits the collimator at a first exit angle; and illuminating the input of the hyperbolic paraboloid aperture with illuminating radiation from a second illumination angle, the second illumination angle different from the first illumination angle, such that a portion of the illuminating radiation passes through the collimator and exits the collimator at a second exit angle, the second exit angle different from the first exit angle, such that radiation exiting the collimator at the first angle and at the second angle irradiate the target.

9. The method of irradiating a target with a collimated beam of radiation according to claim 8, wherein providing a collimator includes proving a collimator having:

an input plate having an first face and a second face, and an first elongated aperture completely through the input plate between the first face and the second face; and an output plate having a third face and a fourth face, and an second elongated aperture completely through the output plate between the third face and the fourth face, the first face parallel to the fourth face, and separated from the fourth face by a predetermined distance, such that a projection of the first elongated aperture intersects the second elongated aperture at a non-zero angle, and such that the intersection of the projection of first elongated aperture and the second elongated aperture forms a rhombus-shaped aperture through which radiation may pass without contacting the input plate and without contacting the output plate.

10. The method of irradiating a target with a collimated beam of radiation according to claim 8, wherein providing a collimator includes proving a collimator having:

a first member comprising a first surface, the first surface being one of a hyperbolic paraboloid surface or a modified hyperbolic paraboloid surface; and a second member comprising a second surface, the second surface being one of a hyperbolic paraboloid surface or a modified hyperbolic paraboloid surface;

the first member disposed relative to the second member such that the first surface faces the second surface, the first surface and second surface separated by a gap so as to define a hyperbolic paraboloid aperture through the collimator.

11. The method of irradiating a target with a collimated beam of radiation according to claim 8, wherein the collimated beam exiting the collimator at the first angle has a first shape in cross-section, and the collimated beam exiting the collimator at the second angle has a second shape in cross-section, the second shape different than the first shape.

12. A system for producing a steerable beam of radiation, comprising:

radiation source means for producing an electronically steerable point source of illuminating radiation; and collimating means having an aperture configured to pass a portion of illuminating radiation incident on said collimating means the collimating means comprising:

a first member comprising a first hyperbolic paraboloid surface; and a second member comprising a second hyperbolic paraboloid surface;

wherein the first member is disposed, relative to the second member, such that the first hyperbolic paraboloid surface is disposed opposite the second hyperbolic paraboloid surface such that the first hyperbolic paraboloid surface is separated from the second hyperbolic paraboloid surface by an aperture gap, such that the first member and second member form the aperture across the aperture gap;

the radiation source means disposed, relative to the collimating means, so as to remain stationary with respect to the collimating means, and so as to illuminate the aperture with incident radiation from the steerable point source of radiation, such that the aperture produces a steerable beam of radiation.

13. The system of claim 12, wherein the radiation source means comprises an electron source and an anode, the electron source configured to illuminate the anode with a steerable electron beam.

14. A system for producing a steerable beam of radiation, comprising:

radiation source means for producing an electronically steerable point source of illuminating radiation; and collimating means having an aperture configured to pass a portion of illuminating radiation incident on said collimating means the collimating means comprising:

a first member comprising a first modified hyperbolic paraboloid surface; and a second member comprising a second modified hyperbolic paraboloid surface;

wherein the first member is disposed, relative to the second member, such that the first modified hyperbolic paraboloid surface is disposed opposite the second modified hyperbolic paraboloid surface such that the first modified hyperbolic paraboloid surface is separated from the second modified hyperbolic paraboloid surface by an aperture gap, wherein the aperture gap is not constant, such that the first member and second member form the aperture across the aperture gap;

the radiation source means disposed, relative to the collimating means, so as to remain stationary with respect to the collimating means, and so as to illuminate the aperture with incident radiation from the steerable point source of radiation, such that the aperture produces a steerable beam of radiation.

15. The system of claim 14, wherein the collimating means comprises a helically cut cylinder.

16. The system of claim 14, wherein the radiation source means comprises an electron source and an anode, the electron source configured to illuminate the anode with a steerable electron beam.

* * * * *

UNITED STATES PATENT AND TRADEMARK OFFICE
CERTIFICATE OF CORRECTION

PATENT NO. : 9,117,564 B2  
APPLICATION NO. : 13/933601  
DATED : August 25, 2015  
INVENTOR(S) : Rommel

Page 1 of 1

It is certified that error appears in the above-identified patent and that said Letters Patent is hereby corrected as shown below:

IN THE CLAIMS  
In Col. 14, line 29  
replace "com risin"  
with "comprising"

In Col. 14, line 29  
replace "surface the"  
with "surface, the"

Signed and Sealed this  
First Day of March, 2016

Michelle K. Lee  
*Director of the United States Patent and Trademark Office*